(12) United States Patent
Rowe et al.

(10) Patent No.: US 9,504,571 B2
(45) Date of Patent: Nov. 29, 2016

(54) SYSTEMS FOR IMPLANTING ANNULOPLASTY RINGS WITH MICROANCHORS

(71) Applicant: Edwards Lifesciences Corporation, Irvine, CA (US)

(72) Inventors: Stanton J. Rowe, Newport Coast, CA (US); Alexander J. Siegel, Newport Beach, CA (US); Ralph Schneider, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 724 days.

(21) Appl. No.: 13/910,975

(22) Filed: Jun. 5, 2013

(65) Prior Publication Data

US 2013/0331930 A1   Dec. 12, 2013

Related U.S. Application Data

(60) Provisional application No. 61/656,810, filed on Jun. 7, 2012.

(51) Int. Cl.
*A61F 2/24* (2006.01)
*A61B 17/04* (2006.01)
*A61B 17/00* (2006.01)

(52) U.S. Cl.
CPC ......... *A61F 2/2466* (2013.01); *A61B 17/0401* (2013.01); *A61F 2/2448* (2013.01); *A61B 2017/00243* (2013.01); *A61B 2017/0409* (2013.01); *A61B 2017/0412* (2013.01); *A61B 2017/0414* (2013.01); *A61B 2017/0427* (2013.01); *A61B 2017/0464* (2013.01); *A61B 2017/0472* (2013.01)

(58) Field of Classification Search
CPC ............... A61B 17/0401; A61B 2017/00243; A61B 2017/0409; A61B 2017/0414; A61B 2017/0427; A61B 2017/0464; A61F 2/2466; A61F 2/2445; A61F 2/2448
USPC ....................................................... 623/2.11
See application file for complete search history.

(56) References Cited

U.S. PATENT DOCUMENTS

| | | | |
|---|---|---|---|
| 3,753,438 A | 8/1973 | Wood et al. |
| 3,857,396 A | 12/1974 | Hardwick |
| 3,910,281 A | 10/1975 | Kletschka et al. |
| 3,976,079 A | 8/1976 | Samuels et al. |
| 4,291,698 A | 9/1981 | Fuchs et al. |
| 4,387,489 A | 6/1983 | Dudek |
| 4,750,492 A | 6/1988 | Jacobs |

(Continued)

*Primary Examiner* — Katherine M Shi
(74) *Attorney, Agent, or Firm* — David L. Hauser

(57) ABSTRACT

Disclosed systems for implanting annuloplasty rings and other prosthetic devices can comprise a plurality of microanchors, sutures threaded through the microanchors, the sutures passing through the prosthetic device, individual microanchor guides, such as tubes or spears, for each microanchor that contain the microanchors during delivery and allow for positioning and deployment of the microanchors into annular tissue. The systems can also comprise a bracket that is temporarily coupled to the prosthetic device, holds the plurality of microanchor guides in position relative to one another and relative to the prosthetic device, and/or guides the sutures passing through the prosthetic device. The prosthetic device can include suture locking mechanisms to secure the prosthetic device to the sutures and to the implanted microanchors after the deployment devices have been removed.

21 Claims, 8 Drawing Sheets

(56) References Cited

U.S. PATENT DOCUMENTS

| | | |
|---|---|---|
| 4,969,892 A | 11/1990 | Burton et al. |
| 5,078,731 A | 1/1992 | Hayhurst |
| 5,282,832 A | 2/1994 | Toso et al. |
| 5,409,499 A | 4/1995 | Yi |
| 5,474,572 A | 12/1995 | Hayhurst |
| 5,514,159 A | 5/1996 | Matula et al. |
| 6,074,409 A | 6/2000 | Goldfarb |
| 8,277,502 B2 | 10/2012 | Miller et al. |
| 8,323,334 B2 | 12/2012 | Deem et al. |
| 8,333,777 B2 | 12/2012 | Schaller et al. |
| 8,715,343 B2 * | 5/2014 | Navia ............... A61F 2/2427 623/2.11 |
| 2008/0281356 A1 | 11/2008 | Chau et al. |
| 2012/0203332 A1 * | 8/2012 | Navia ............... A61F 2/2427 623/2.11 |

* cited by examiner

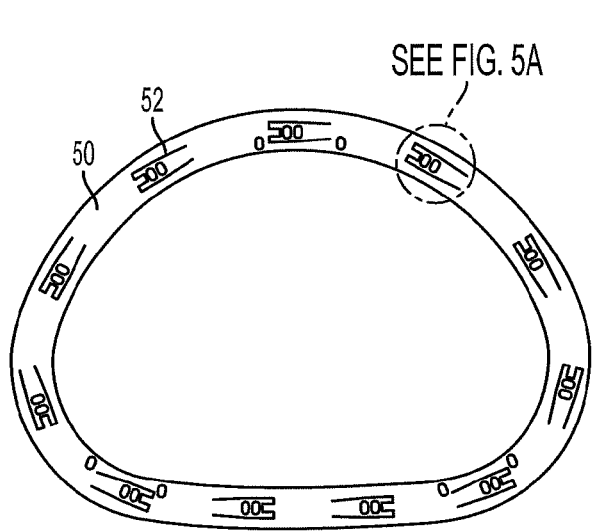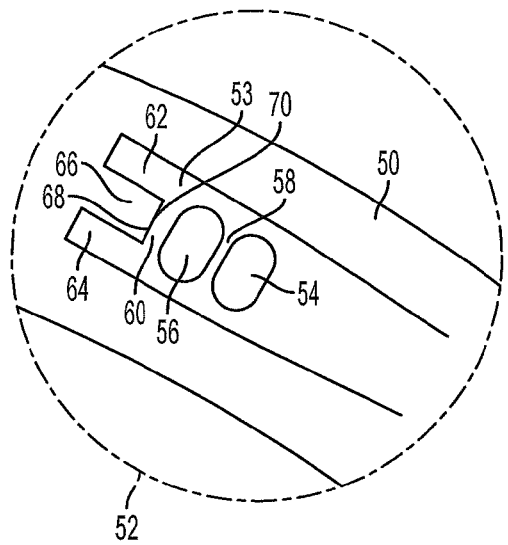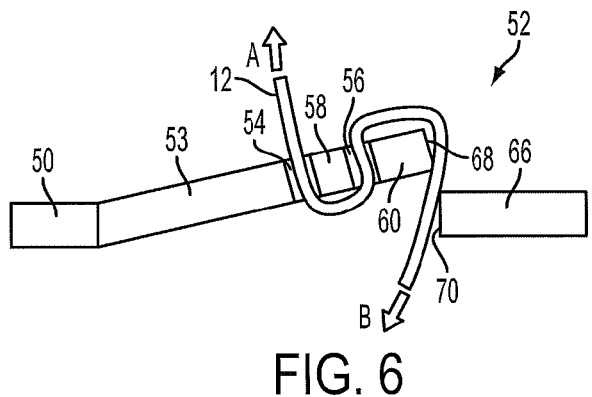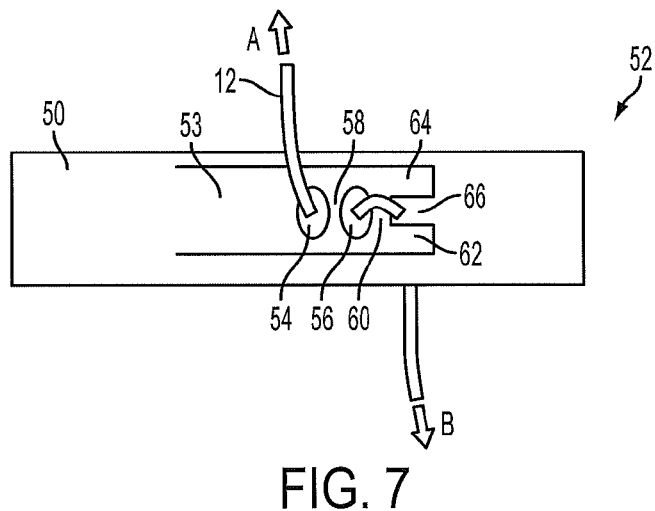

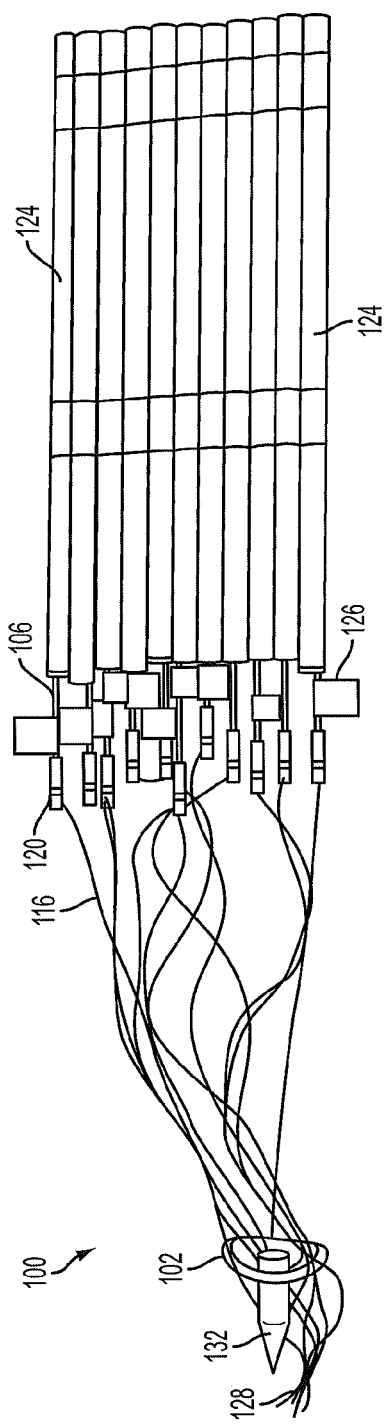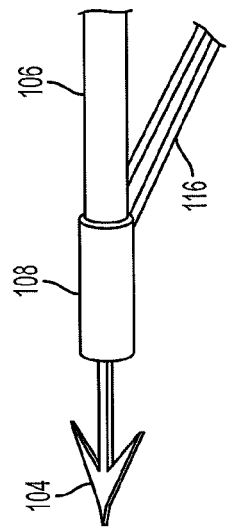
FIG. 8
FIG. 9
FIG. 10

SYSTEMS FOR IMPLANTING ANNULOPLASTY RINGS WITH MICROANCHORS

CROSS REFERENCE TO RELATED APPLICATION

This application claims the benefit of U.S. Provisional Patent Application No. 61/656,810, filed on Jun. 7, 2012, which is incorporated by reference herein.

BACKGROUND

In the anatomy of the human heart, the left atrium receives oxygenated blood from the lungs through the pulmonary veins. The mitral valve separates the left atrium from the left ventricle. The mitral annulus comprises a fibrous ring encircling the orifice between the left atrium and the left ventricle. The mitral valve is a bicuspid valve having a posterior leaflet that cooperates with an anterior leaflet. During diastole, as the contraction triggered by the sinoatrial node progresses through the atria, oxygenated blood passes through the mitral valve into the left ventricle. In this phase, the aortic valve leading into the ascending aorta closes, allowing the left ventricle to fill with blood. A similar flow of venous blood occurs from the right atrium through the pulmonary valve to the right ventricle. Once the ventricles are full, they contract during the systolic phase and pump blood out of the heart. During systole, the mitral valve closes and the aortic valve opens, thus preventing blood from regurgitating into the left atrium and forcing blood into the aorta, and from there throughout the body. Because of the high pressures associated with the left ventricle during systole, proper functioning of the mitral valve to prevent blood from flowing back through the system is extremely important.

In many developed countries, congestive heart failure is a leading cause of hospitalization and death, and its incidence is increasing. When imperfections in the mitral valve allow blood to flow backward into the left atrium, known as mitral regurgitation, the left ventricle must pump progressively harder to circulate blood throughout the body, which in turn promotes congestive heart failure. Heart transplantation is considered a standard treatment for select patients with severe congestive heart failure and end-stage heart disease, but only a small number of donor hearts are available and there are severe surgical risks for weaker patients. Accordingly, alternative medical and surgical strategies are evolving to treat such conditions.

One typical cause of mitral regurgitation is malformation of the mitral annulus, such as due to dilation of the left ventricle. Malformation of the mitral annulus can cause the mitral leaflets to not coapt properly, thereby allowing blood to flow back into the left atrium. Stabilizing and restructuring the mitral annulus can allow the mitral leaflets regain their proper function and eliminate or reduce mitral regurgitation.

Various interventions have been used to alter the size and shape of the regurgitant orifice area. Annuloplasty rings have been developed in various shapes and configurations over the years to correct mitral regurgitation and other conditions which reduce the functioning of the valve. For example, Carpentier, et al. in U.S. Pat. No. 4,055,861 disclosed two semi-rigid supports for heart valves, one of which being closed (or D-shaped) and the other being open (or C-shaped). Some annuloplasty rings are contoured to conform to an abnormal posterior aspect, or other portion, of the mitral annulus, such as is disclosed by McCarthy in U.S. Pat. No. 7,608,103. A variety of other styles of annuloplasty rings are also known.

Typically, annuloplasty rings, regardless of the style, are implanted via open heart surgery through the left atrium and are fixed to the mitral annulus or surrounding tissue with a plurality of sutures disposed radially around the perimeter of the ring and attached to a sewing sheath surrounding the ring. The sutures typically pull the mitral annulus radially inwardly toward the ring to reduce the diameter and/or reshape the mitral annulus.

SUMMARY

Disclosed herein are systems and methods for implanting an annuloplasty ring or other prosthetic device, at the mitral annulus. Disclosed systems can comprise a plurality of microanchors, sutures threaded through the microanchors, the sutures passing through the prosthetic device, individual microanchor guides, such as tubes or spears, for each microanchor that contain the microanchors during delivery and allow for positioning and deployment of the microanchors into annular tissue. The systems can also comprise a bracket that is temporarily coupled to the prosthetic device, holds the plurality of microanchor guides in position relative to one another and relative to the prosthetic device, and/or guides the sutures passing through the prosthetic device. The prosthetic device can include suture locking mechanisms to secure the prosthetic device to the sutures and to the implanted microanchors after the deployment devices have been removed.

Some exemplary systems comprise an annuloplasty ring, a tube passing through an opening in the annuloplasty ring, a microanchor disposed within the tube, and a plunger disposed at least partially in the tube and configured to push the microanchor out of the tube for implantation of the microanchor into the mitral annulus or other tissue adjacent the mitral annulus. The system can further comprise a suture coupled to the microanchor and threaded through the tube.

In some embodiments, the system can comprise a plurality of microanchors disposed in a plurality of respective tubes that pass through a plurality of respective openings in the ring, and a plurality of plungers disposed at least partially in the respective tubes. For example, the plurality of tubes can be connected together with a bracket above the ring, such as above the top ends of the tubes.

In some embodiments, the microanchor comprises a stop to control to depth of implantation into tissue. In some embodiments, the microanchor can be less than 12 mm in length.

In some embodiments, the tube can be rotatable relative to the ring. In some embodiments, the tube and plunger are removable from the ring after the microanchor is implanted. The plunger can comprise an inner lumen and the sutures can extend through the inner lumen. In some embodiments, the tube can be curved along its longitudinal axis.

An exemplary method of implanting an annuloplasty ring comprises: positioning an annuloplasty ring adjacent to the native mitral annulus, and after positioning the annuloplasty ring, deploying microanchors into tissue of, or adjacent to, the native mitral annulus to secure the annuloplasty ring to the tissue, wherein deploying the microanchors comprises pushing the microanchors out of a plurality of respective, discrete microanchor holders that pass through or adjacent to the annuloplasty ring.

In some embodiments, pushing a respective microanchor comprises moving a plunger within the tube such that an end of the plunger pushes the microanchor out of the tube.

In some embodiments, the method can further comprise pulling the tube out of the annuloplasty ring after the microanchors are deployed in the tissue and sutures coupled to the microanchor pass through openings in the ring. The method can further comprise pulling the sutures relative to the ring to pull the annular tissue toward the ring to correct the shape of the annulus and/or securing the sutures to the ring to retain the annular tissue in a corrected shape. Pulling the sutures can comprise pulling the sutures through a plurality of openings in the ring that are coupled to a plurality of microanchors implanted in the tissue. For example, pulling the plurality of sutures may be performed simultaneously with a single tool. In some embodiments, securing the sutures to the ring comprises advancing a clip down the suture and engaging the clip to the suture and the ring.

In some embodiments, positioning the annuloplasty ring adjacent to the native mitral annulus comprises positioning a ring holder coupled to the annuloplasty ring adjacent to the native mitral annulus, the ring holder comprising a plurality microanchor holder guides configured to guide the microanchor holders and a plurality of suture guides configured to guide the sutures from the annuloplasty ring through the ring holder.

Exemplary suture locking mechanisms for an annuloplasty ring can comprise at least one flap that is bendable out of plane from a surrounding portion of an annuloplasty ring, the flap comprising a first hole, a second hole, and a first surface that is positioned adjacent to a second surface on the ring. The flap can be configured to receive a suture extending through the first and second holes and between the first and second surface, such that tension in an engaged portion of the suture extending from between the first and second surfaces causes the first and second surfaces to grip the suture and prevent the suture from sliding between the first and second surfaces, and such that tension in a free end of the suture extending from the first hole causes the first and second surfaces to separate from one another to allow the suture to slide between the first and second surfaces.

In some embodiments, the at least one flap comprises plural flaps. In some embodiments, the flap is laser cut in the annuloplasty ring. In some embodiments, the flap is configured to lock a suture with the engaged portion of the suture engaged in adjacent tissue extending to the first and second surfaces, and a second portion of the suture extending from the first and second surfaces, through the first and second openings, and to the free end of the suture. In some embodiments, the flap further comprises first and second end portions that extend past the first surface to prevent the suture from sliding off the first surface.

Exemplary systems for implanting an annuloplasty ring at the mitral annulus can comprise a bracket, an annuloplasty ring coupled to the bracket, a plurality of elongated spears coupled to the bracket, a plurality of microanchors coupled to an end the spears, and a plurality of sutures, at least one of the sutures attached to each microanchor, the sutures extending from the respective microanchor, through the annuloplasty ring, and through the bracket.

In some embodiments, each spear comprises a pusher at a second end opposite from the respective microanchor, each pusher configured to deploy the respective microanchor from the spear by moving the pusher in the direction of the microanchor.

In some embodiments, the bracket comprises a plurality of tubular spear holders, one of the spear holders being positioned around a portion of each spear.

In some embodiments, the annuloplasty ring comprises a suture locking mechanism comprising at least one flap that is bendable out of plane from a surrounding portion of the annuloplasty ring, the flap comprising a first hole, a second hole, and a first surface that is positioned adjacent to a second surface on the annuloplasty ring, and at least one of the sutures passes through the suture locking mechanism.

In some embodiments, the bracket comprises an annuloplasty ring holder releasably coupled to the annuloplasty ring.

In some embodiments, the bracket comprises a plurality of distal suture guides, one for each microanchor, and a proximal suture guide configured to guide the sutures from the microanchors through the bracket.

In some embodiments, each spear is supported by the bracket at two discrete locations. In some embodiments, each spear is rotatable and longitudinally slidable relative to the bracket while being supported by the bracket. In some embodiments, each spear is laterally detachable from the bracket.

In some embodiments, each suture extends from the respective microanchor, through a suture lock in the annuloplasty ring, and through at least one suture guide in the bracket. The system can further comprise a proximal handle coupled to the bracket, with each suture extending from the at least one suture guide through a passageway in the proximal handle.

In some embodiments, the system comprises plural spears supported by the bracket, each spear having a microanchor coupled to a distal end of the spear; the system comprises at least one suture for each microanchor, the annuloplasty ring comprises a discrete suture lock for each microanchor, the bracket comprises a discrete suture guide for each suture lock and further comprises a common suture guide proximal to the discrete suture guides, and the system comprises a proximal handle having a passageway extending therethrough. Each suture can extend from the respective microanchor, through a respective suture lock, through a respective suture guide, through the common suture guide, and through the passageway in the handle.

The foregoing and other objects, features, and advantages of the disclosed technology will become more apparent from the following detailed description, which proceeds with reference to the accompanying figures.

BRIEF DESCRIPTION OF THE DRAWINGS

FIG. 5 is a plan view of an exemplary annuloplasty ring comprising suture locks.

FIG. 5A is an enlarged view of a portion of the ring of FIG. 5 showing one of the locks.

FIG. 6 is a cross-sectional side view of a suture lock engaged with a suture.

FIG. 7 is a plan view of a suture lock engaged with a suture.

FIG. 8 shows an exemplary embodiment of another system for implanting an annuloplasty ring.

FIG. 9 shows an exemplary spear of the system of FIG. 8.

FIG. 10 shows a microanchor and adapter coupled to the distal end of the spear of FIG. 9.

DETAILED DESCRIPTION

Exemplary suturing methods and related apparatuses are disclosed herein to facilitate implantation of a prosthetic device using microanchors. The detailed description proceeds with reference to implantation of an annuloplasty ring. However, the methods and related apparatuses disclosed herein can also be used to implant valves, stents, and similar devices within the body, and in particular, prosthetic heart valves within the native valve annuluses of the heart.

Figure 1:
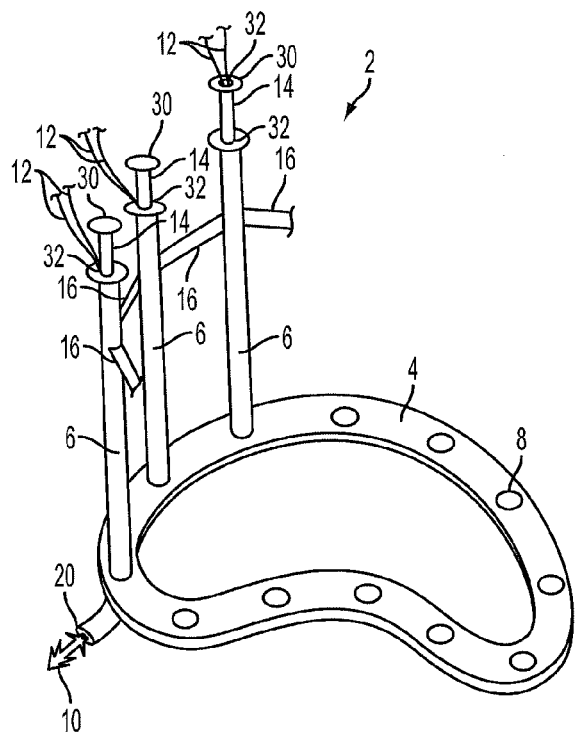
FIG. 1 is a perspective view of an exemplary system for implanting an annuloplasty ring. Some portions of this system are not shown in this view for illustrative purposes.

FIG. 1 shows an exemplary apparatus 2 for implanting an annuloplasty ring at the mitral annulus MA. The apparatus can comprise an annuloplasty ring 4, plural guide tubes 6 passing through openings 8 in the ring, microanchors 10 disposed within the tubes, sutures 12 coupled to the microanchors and extending upwardly through the tubes, and plungers 14 (also referred to as pushers) disposed within the tubes and configured to push the microanchors out of the lower ends of the tubes. The tubes 6 can be attached together by one or more brackets 16.

The ring 4 can comprise a semi-rigid ring made from materials such as Elgiloy (an alloy of cobalt, nickel and other metals), titanium, or stainless steel. In other embodiments, the ring can be a foldable ring with micro-hinges such that the ring can be folded open within the left atrium and locked in the open configuration. In other embodiments, the ring can comprise shape memory material, such as Nitinol, that is more collapsible for percutaneous delivery.

The ring 4 can have any of various suitable shapes. For example, the ring 4 can be generally kidney-shaped as shown in FIG. 1, or can be generally D-shaped, as shown and described in U.S. Pat. Nos. 7,608,103 and 7,294,148, which are incorporated herein by reference.

Figure 2:
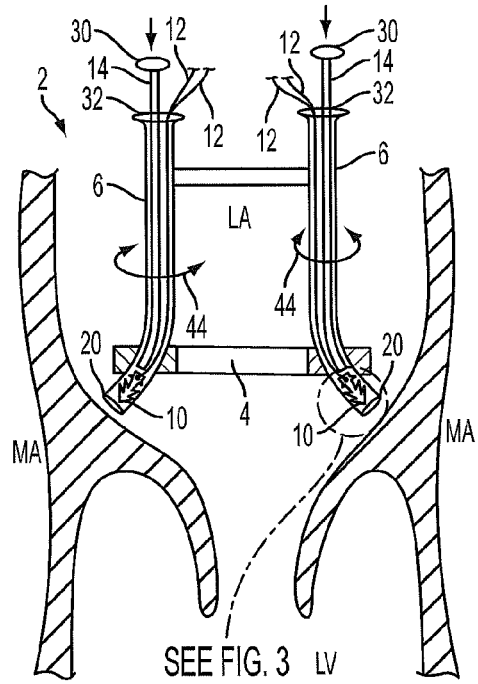
FIG. 2 is a cross-sectional view of the mitral valve region with the system of FIG. 1 in a position ready to implant an annuloplasty ring.

The tubes 6 can be rigid or semi-rigid and can comprise a curved lower portion 6a that passes through the openings 8 in the ring 4 and curves radially outwardly such that the lower ends of the tubes are directed at angle, such as about 45°, towards the mitral annulus or surrounding tissue during implantation, as shown in FIG. 2. The tubes 6 can also be individually rotatable about their vertical axes relative to the ring 4 and the bracket 16 (in the directions indicated by arrows 44) in order for the lower outlet of the tubes to be directed in a desired direction.

The apparatus 2 can comprise any number of sets of tubes 8, plungers 14 and microanchors 10, such as from 5 to 15 sets, disposed around the ring, desirably at about equal spacing. The ring 4 can likewise have any number of openings 8, though the number of openings should be equal to or greater than the number of tubes 8. Only three tubes 6 are shown in FIG. 1 for illustrative purposes, though most or all of the openings 8 would typically include tubes 6 such that the ring 4 can be securely anchored to the mitral annulus at several points around the ring.

Figure 3:
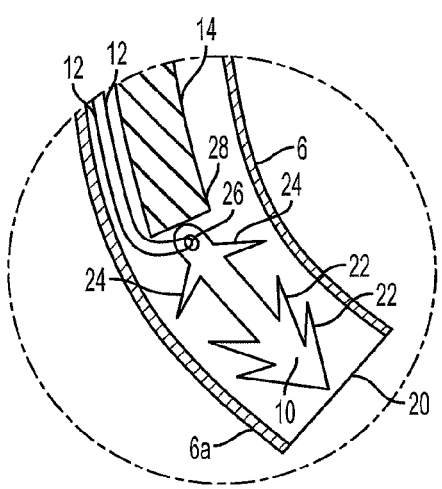
FIG. 3 is an enlarged cross-sectional view of a portion of FIG. 2.

As shown in FIG. 3, the microanchors 10 can be positioned within the tubes 6 near the lower outlets 20 of the tubes. The microanchors 10 can comprise rigid material, such as metallic, polymeric, or ceramic materials. The microanchors 10 can be about 2 mm to about 12 mm in length and can comprise one or more sets of barbs 22 for anchoring into the tissue of and around the mitral annulus. The microanchors 10 can also comprise stops 24, which can control the depth of implantation into the tissue and can prevent or reduce migration of the microanchors. The tails of the microanchors 10 can comprise openings 26 for coupling sutures 12 to the microanchors. The sutures 12 can comprise one or more strands threaded through the openings 26 and threaded upwardly through the tubes 6.

In some embodiments, the microanchors 10 can be positioned partially or completely outside of the tubes 6, rather than inside the tubes, in preparation for tissue engagement. In one example, the microanchors 10 can partially extend out of the lower outlets 20 of the tubes. In another example, the microanchors 10 can be positioned just outside of the lower outlets 20 of the tubes. The microanchors 10 can be held in place against the lower outlets 20 with tension from the sutures 12.

The plungers 14 can comprise lower ends 28 disposed within the tubes 6 and configured to contact the tails of the microanchors 10 to push the microanchors out of the lower ends of the tubes. The plungers 14 can further comprise upper ends 30 that extend out of the top openings 32 of the tubes 6. The upper ends 30 of the plungers can be moved toward the top openings 32 of the tubes to cause the lower ends 28 to push the microanchors out of the tubes and into the tissue. The distance between the upper ends 30 of the plungers and the top openings 32 of the tubes can be adjusted to control the depth of implantation of the microanchors 10. In some embodiments (not shown), the upper ends 30 of the plungers 14 can be connected together, such as with a bracket, to present a stable base such that all of the plungers 14 can be pushed together in order to deploy the microanchors 10 at the same time. In another example, each of the microanchors 10 can be deployed individually, such as by holding the top of a tube 6 with two fingers and pushing the plunger 14 with a thumb, similar to syringe. In another example, the pushing mechanism can be hydraulic (e.g., using saline pressure to drive the plunger). The upper ends 30 of the plungers can be about 3 to about 9 inches above the ring 4.

In some embodiments, the plungers 14 can comprise an inner lumen through which the sutures 12 can be threaded. An exemplary plunger lumen 32 is shown in FIG. 1 with the sutures 12 extending out of the top of the plunger lumen. Though only one of the plungers 14 in FIG. 1 is shown with a plunger lumen 32 for illustration, typically all or none of the plungers 14 would comprise a lumen 32. Particularly in embodiments where the sutures 12 pass up through a plunger lumen, the lower end of the plunger can comprise an enlarged end (not shown) that fits snugly within the tube 6. The enlarged end can seal off the portion of the tube 6 above it such that blood cannot pass between the plunger and the tube. The enlarged end can also improve contact between the plunger and the tail of the microanchor 10. In some embodiments, the intermediate portion of the plunger can comprise a wire or other semi-flexible component that is capable of transferring axial pushing force from the upper end 30 of the plunger to the lower end 28, but is also flexible enough to bend around the gradual curve in the lower portion of the tubes 6.

Figure 4:
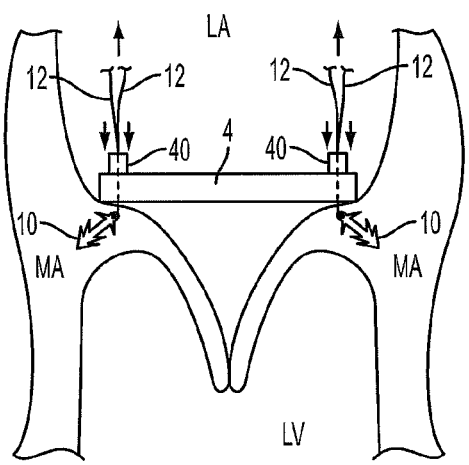
FIG. 4 is a side view of the mitral valve region after the annuloplasty ring is been implanted.

As shown in FIG. 2, the apparatus 2 can be positioned in the left atrium LA above the mitral annulus MA such that the lower ends 20 of the tubes 6 are adjacent to the mitral annulus. The tubes 6 can then be individually rotated such that each of them is desirably oriented toward the implantation site. The plungers 14 can then be pushed relative to the tubes 6 to deploy the microanchors 10. After the microanchors 10 are pushed into the tissue, as shown in FIG. 4, the tubes 6 and the plungers 14 can be pulled upwardly such that the lower ends of the tubes and plungers slide out of the openings 8 in the ring 4 and over to the top ends of the sutures 12. At this stage, the microanchors 10 are implanted in the tissue and the ring 4 is positioned freely in the left atrium with the sutures 12 passing through the openings 8.

The sutures 12 can be pulled, as a group or individually, relative to the ring 4 to pull the tissue toward the ring to reshape the annulus as needed. In some embodiments, a device can be used to grasp and pull all of the sutures 12 at the same time and/or at the same rate or distance, especially if annular diameter reduction is planned.

As shown in FIG. 4, the top ends of the sutures 12 can be held taught while clips 40 are positioned around the sutures and advanced down against the top of the ring 4. The sutures 12 can then be pulled upwardly while the clips 40 and the ring 4 are pushed downwardly against the mitral annulus, or alternatively held in place, to pull the mitral annulus inward and/or toward the ring to correct the shape of the annulus. The clips 40 can then be fixedly secured to the sutures 12 and the free ends of the sutures can be cut off. Each of the sutures can be individually tightened and clipped or all can be tightened and clipped at the same time.

Exemplary clips, systems for deploying the clips and cutting the sutures, and related methods are described in U.S. Pat. App. Pub. No. 2008/0281356, which is incorporated by reference herein. Various other types of suture fastening techniques and mechanisms can also be used in other embodiments.

In some embodiments, integrated locks or ratcheting mechanisms can be disposed within the openings 8 in the ring 4. The integrated locks or ratcheting mechanisms can allow the sutures 12 to move upwardly though the openings, but prevent the sutures from moving downwardly through the openings. This can allow the sutures to be pulled through the ring to pull the tissue toward the ring and then keep the sutures from loosening.

After the ring 4 is implanted and the sutures 12 are locked tight, additional microanchors can be deployed to supplement to initially deployed microanchors 10. In some embodiments, the ring 4 can comprise additional openings 8 for this purpose. In other embodiments, the additional microanchors can be attached to a sewing sheath via sutures.

In alternative embodiments, the tubes 6 can have other shapes. For example, the tubes 6 may not be curved in some embodiments, and instead the tubes 6 can be straight tubes that extend through the ring at an angle, such as at about 45°, so that the lower ends of the tubes direct the microanchors into the surrounding tissue.

In some embodiments, instead of the tubes 6 passing through openings 8 in the core of the ring 4, the tubes can instead pass through only one or more outer layers of the ring, such as silicone or fabric layers that form a sewing sheath, and the sutures can couple the microanchors 10 to these outer layers rather than passing through the more rigid and structural inner material of the ring.

Using the apparatuses, systems and methods disclosed herein, the mitral annulus can be reshaped and resized such that the mitral leaflets properly coapt and the mitral valve properly functions as a one-way valve without regurgitation. The disclosed embodiments can allow for quicker and more accurate implantation of an annuloplasty ring. For example, the ability to deploy all of the microanchors in one motion can save time compared to individually stitching many sutures around the ring. The geometry of the plungers and tubes can also be calibrated to carefully control the depth of insertion of the microanchors for optimal placement in the tissue.

Typically, sutures are secured by tying a knot. However, tying a knot in a suture can be difficult to perform, can be time consuming, and/or can leave more or less slack in the suture than desired. For example, when implanting an annuloplasty ring, it can be difficult to accurately tie knots in the several sutures attaching the ring to the tissue, it can take a significant amount of time to tie all of the knots one at a time, and each of the sutures can be left with unequal amounts of slack. Furthermore, it can be difficult to further tighten a suture after it is knotted if there is too much slack.

FIGS. 5-7 illustrate an exemplary annuloplasty ring 50 that comprises suture locks 52 that can eliminate the need to tie knots in the sutures 12 when implanting the ring. In some embodiments, the ring 50 can comprise a flat sheet of material, such as stainless steel or Nitinol. The sheet can be relatively thinner at least in the areas of the locks 52 (e.g., about 0.010 inch thick) but can be thicker in areas between the locks. In other embodiments, the ring can have a uniform thickness (e.g., about 0.010 inch thick). The ring 50 can be laser cut from a single piece of material. The locks 52 can also be laser cut into the ring 50, or otherwise cut from the same sheet as the rest of the ring, such that the ring 50 and the locks 50 are all part of the same unitary piece of material. In particular embodiments, ring 50 has sufficient rigidity to reshape the valve annulus when secured in place. In other embodiments, the ring 50 can be a relatively thin ring mounted to a more rigid base ring, which can have apertures aligned with the locks 52 through which the sutures can pass.

As shown in FIG. 5, the plural locks 52 can be disposed around the ring 50, such as at evenly spaced intervals. Furthermore, each of the locks 52 can be oriented in the same direction (e.g., all facing clockwise or counterclockwise). The ring 50 can comprise any number of locks 52, such as from 5 to 15, and each lock 52 can be configured to secure a respective one or more sutures 12 coupling the ring 50 to the tissue.

As shown in FIG. 5A, each lock 52 can comprise a flap 53 that is generally centered on a segment of the ring 50 between the outer and inner perimeters of the ring. Each flap 53 can comprise a first hole 54 and a second hole 56 passing through the ring. Each lock flap 53 can comprise a first bridge 58 extending between the first and second holes 54, 56 and a second bridge 60 extending along the opposite side of the second hole 56. Each flap 53 can comprise a first end portion or leg 62 and a second end portion or leg 64 extending past the second bridge 60 and positioned on either side of a tang 66 that extends from the ring apart from the flap 53. The tang 66 has an end surface 70 that is adjacent to a surface 68 of the second bridge 60 of the flap.

As shown in FIGS. 6 and 7, the flap 53 can bend out of plane from the ring 50 such that the end portions 62 and 64 separate from the tang 66 and open a gap between opposing surfaces 68 and 70. A suture 12 can be threaded through the openings 54 and 56 and through the gap between the surfaces 68 and 70 while the flap 53 is bent out of plane from the ring 50. As shown in FIG. 6, the suture 12 can be threaded upwardly from an engaged end B that is engaged with the tissue, between the surfaces 68 and 70, around the upper surface of the second bridge 60, down through the second hole 56, around the lower surface of the first bridge 58, and back up through the first hole 54 to a free end A.

With the suture 12 threaded through the lock 52 as shown in FIG. 6, the suture can be tightened by pulling on free end A of the suture. This upward force on the free end A pulls on the first bridge 58 and causes the flap 53 to bend out of plane from the ring 50, opening the gap between the surfaces 68 and 70 such that the suture 12 is not pinched and can slide through the lock 52.

However, when tension on the free end A of the suture 12 is released, tension in the engaged end B between the tissue and the ring 50 pulls downwardly on the second bridge 60 and pulls the flap 53 back into, or toward, plane with the ring and causes the surfaces 68 and 70 to pinch the suture, which prevents the suture from sliding through the lock 52. Also, downward pressure can be applied directly to the flap 53 to push the flap back into plane with the ring. The lock 52 can grip the suture 12 tighter with increased tension on the engaged end B, creating a self-tightening locking mechanism that prevents the ring 50 from loosening from the tissue after the sutures 12 have been pulled tight. This obviates the need for tying knots in each of the sutures 12 above the ring 50, which reduces the time of the procedure. Furthermore, if a suture 12 is too loose after an initial tightening, the free end A can simply be pulled tighter to reduce the slack in the engaged end B.

The end portions 64 and 62 of the flap 53 can corral the suture 12 between the tang 66 and the second bridge 60 to prevent the suture from sliding off the surfaces 68 and 70 and causing the lock 52 to malfunction.

The ring 50 or just the suture locks 52 can be implemented in the annuloplasty ring 4 described above (FIGS. 1-4) as an alternative to suture clips 40. In one implementation, for example, the ring 4 can be formed with suture locks 52, one for each microanchor 10. A suture 12 connected to a microanchor 10 can be threaded through a side opening in the lower portion of the tube 6 and through a corresponding suture lock 52 in the manner shown in FIGS. 6 and 7. In another implementation, the ring 50 can be mounted on top of the ring 4.

FIG. 8 shows an exemplary embodiment of an alternative system 100 for implanting an annuloplasty 102 ring using microanchors 104.

Figure 11:
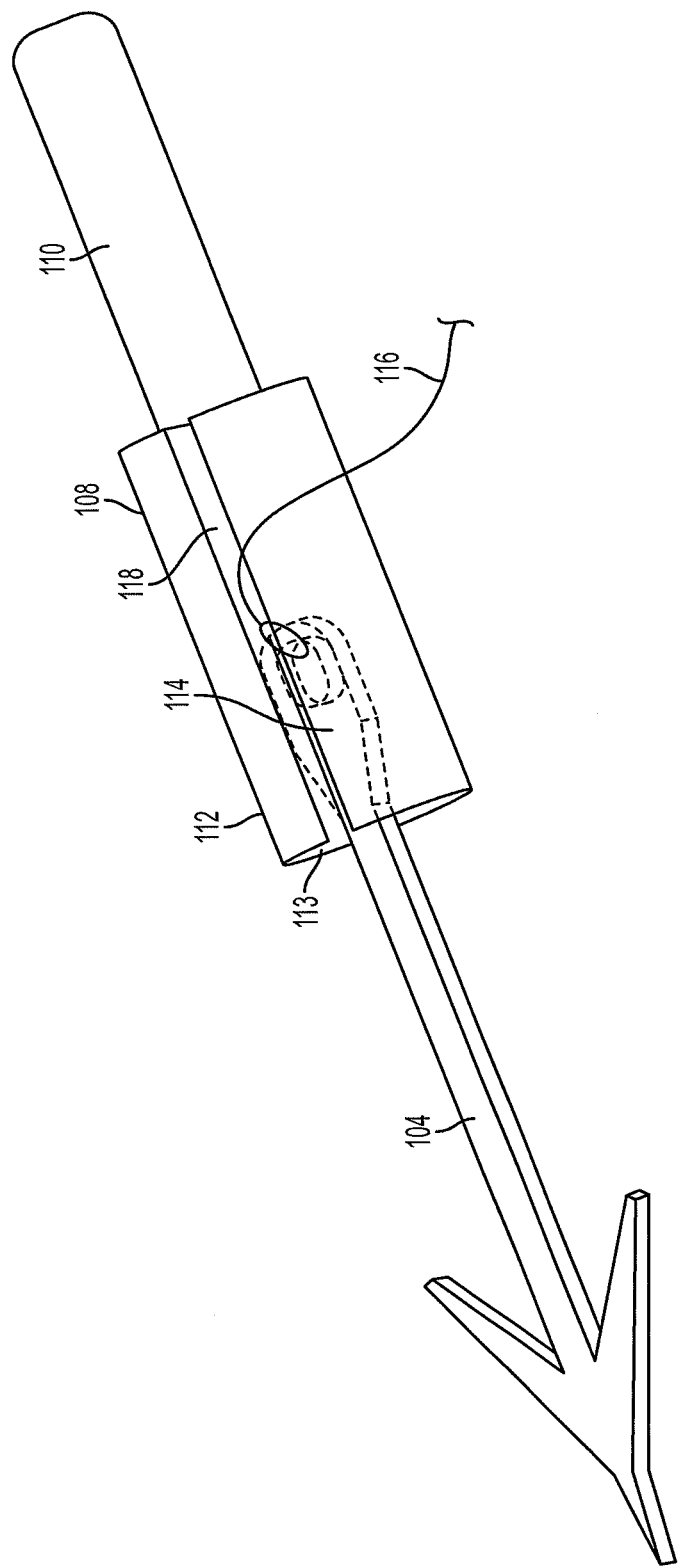
FIG. 11 is another view of the microanchor and adapter of FIG. 10.

The system 100 can comprise a plurality of elongated spears 106 each having a microanchor 104 releasably coupled to a first end of the spear, as shown in FIG. 9. The spears 106 can comprise a rigid tube or rod, such as made of stainless steel. In some embodiments, adapters 108 can be used to couple the microanchors 104 to the spears 106, as shown in FIGS. 10 and 11. The adapter 108 can be attached to the spear 106 in any manner. For example, the end of the spear 106 can comprise a female opening that receives a male portion 110 of the adapter 108. The adapter 108 can further comprise a tubular body 112 having an opening configured to receive a tail end 114 of the microanchor 104 to temporarily couple the microanchor to the spear 106. The tail end 114 of the microanchor is attached to a suture 116. The body 112 of the adapter 108 can comprise a longitudinal slot 118 through which the suture 116 can pass while the microanchor is held in the adapter. In some embodiments, the microanchors 104 can be held directly in a recess at the end of the spears 106, or in other manners excluding the adapters 108. In other embodiments, the structure of the adapter 108 can be integrated into the distal end of the spear 106 in a one piece construction.

Figure 12:
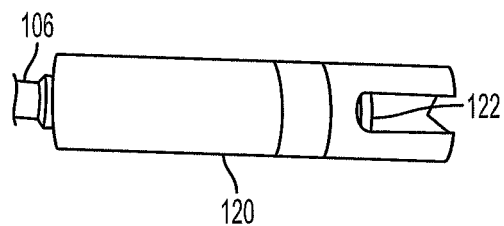
FIG. 12 shows a suture holder coupled to a proximal end of the spear of FIG. 9.

As shown in FIG. 12, each spear 106 can have a suture holder 120 at a second end of the spear opposite from the microanchor 104. The suture 116 can extend from the tail 114 of the microanchor 104, through the slot 118 in the adapter 108, along the outside of the spear 106 and through the suture holder 120. The suture holder 120 can comprise a slit 122 configured to grip the suture 116 strong enough to hold the suture taught between the microanchor 104 and the suture holder 120, yet loose enough to allow the suture to be easily pulled out of slit 122 and without damaging the suture.

As shown in FIG. 8, the system 100 can comprise plural spears 106, each preloaded with a microanchor 104 and a suture 116 engaged in the suture holder 120. For example, the illustrated system includes 11 such preloaded spears 106. Each spear 106 can be stored and/or held in a tube 124 prior to use. The plural tubes 124 can be attached together, such as in a flat pattern such as is shown in FIG. 8 or in a ring pattern or other configuration for ease of handling, storage, transportation, etc. Each of the spears 106 can further be numbered for reference, such as with a tag 126. As shown in FIG. 8, the spears 106 are labeled 1 through 11. The reference number can indicate the location around the annulus where that particular microanchor should be implanted and/or the sequential order in which the microanchors should be implanted.

Figure 13:
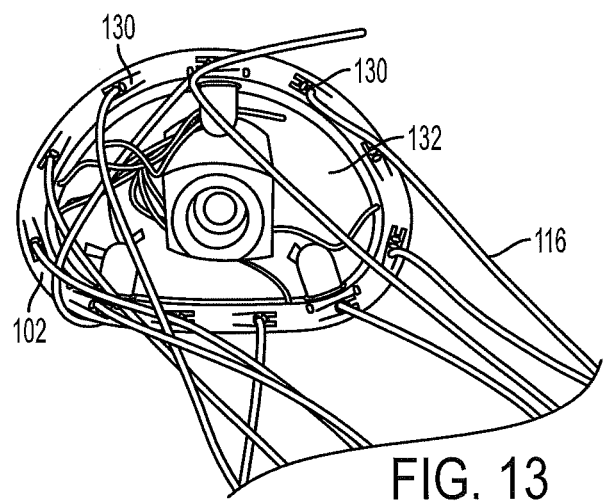
FIG. 13 shows an annuloplasty ring coupled to a ring holder with sutures passing through suture locks in the ring.

As shown in FIG. 8, after passing through the suture holders 120, the sutures 116 pass through the annuloplasty ring 102 and are collected together at their free ends 128. As shown in FIG. 13, the sutures extend from the suture holders 120 through suture locks 130 in the ring 102. The suture locks 130 allow the sutures to move through the ring 102 only in one direction and prevent the sutures from moving in the opposite direction through the ring. The suture locks 130 can be similar to the suture locks 52 described above and the ring 102 can be similar to the ring 50 described above. With reference to FIG. 8, the suture locks 130 allow the ring 102 to move to the right, toward the spears 106, along the sutures 116, but prevent the ring from sliding along the sutures to the left toward the free ends 128 of the sutures.

The annuloplasty ring 102 can be coupled to a ring holder 132 for ease of handling. The holder 132 can attach to the inner periphery of the ring 102, such as with temporary sutures, such that the holder can be easily removed from the ring after the ring is implanted.

With the system 100 in the configuration shown in FIG. 8, the ring 102 can be ready to be implanted, such as at a mitral annulus. Each of the spears 106 can be individually removed from its tube 124 for use. The spear 106 is retracted from the tube 124 in the direction of the suture holder 120. The spear 106, with the suture 116 tethering it to the ring 102, is then inserted into the patient and the barbed end of the microanchor 104 is implanted into the tissue at a desired location. The distal surface 113 of the adapter body 112 can act as a stop to control the depth of insertion of the microanchor 104 into the tissue. Also, the depth of the opening inside the adapter body 112 can determine how deep the tail 114 sits in the adapter 108 can control the depth of insertion of the microanchor. The reference number on the tag 126 can indicate which spear 106 is used first and/or the location around the annulus where the corresponding microanchor 104 is to be implanted. Once the microanchor is implanted in the tissue, the spear 106 can be retracted in order to dislodge the tail 114 of the microanchor from the adapter 108, and thus from the spear 106. The suture 116 can also be removed from the slit 122. The spear 106 is then free from the microanchor and the suture and be discarded or otherwise removed, leaving the suture 116 extending from the implanted microanchor 104 out of the patient to the yet to be implanted ring 102. Each of the microanchors 104 can be implanted in the same way.

After all of the microanchors are implanted around the annulus, the ring 102 can be slid along the sutures 116, such as be holding the free ends 128 of the sutures taught, into the patient and into position against the annulus. Each of the sutures 116 can be independently tightened by pulling the suture a desired amount through the suture locks 130 to pull the annular tissue toward the line locks and reshape the annulus as desired.

After the ring 102 is implanted at the annulus, the free ends 128 of the sutures can be cut off and the ring holder 132 can removed from the ring and retracted out of the patient.

This system 100 and the corresponding methods of use can allow a surgeon greater flexibility in the timing and location of the implantation of each microanchor. Instead of inserting all of the spears into the annular region at the same time in a bracketed delivery apparatus, the system 100 allows each spear to be inserted and removed from the body one at a time. The system 100 allows each microanchor 104 to be implanted at any location relative to the other microanchors, as opposed to having the relative position of the spears fixed by a bracketed delivery apparatus. This can be particularly advantageous for use with an irregularly shaped annulus and/or for clustering some of the microanchors in a certain area of the annulus. The ability to implant each spear/microanchor individually also allows for a smaller incision through the body and into the heart, minimizing damage to the patient. The size of the incision can be limited by the minimum size of the ring 102, rather than the size of the bracketed delivery apparatus. Where the ring is flexible, the incision can be made even smaller. However, managing the sutures 116 can pose a challenge, as the free lengths of the sutures 116 between the microanchor 104 and the suture lock 120 and between the suture lock and the ring 102 can become tangled or caught on other equipment.

Figure 14:
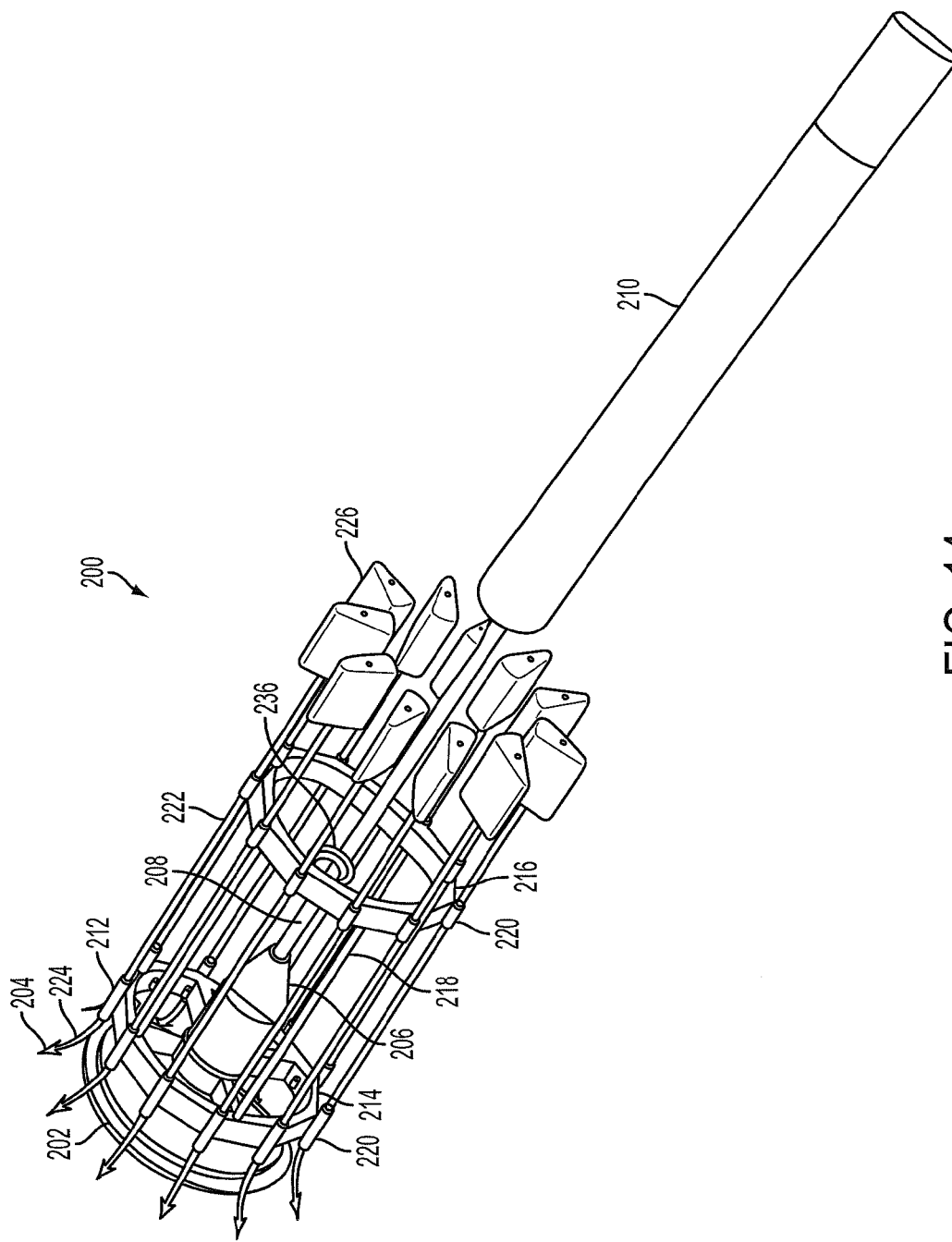
FIGS. 14-16 show an exemplary embodiment of another system for implanting an annuloplasty ring.
Figure 15:
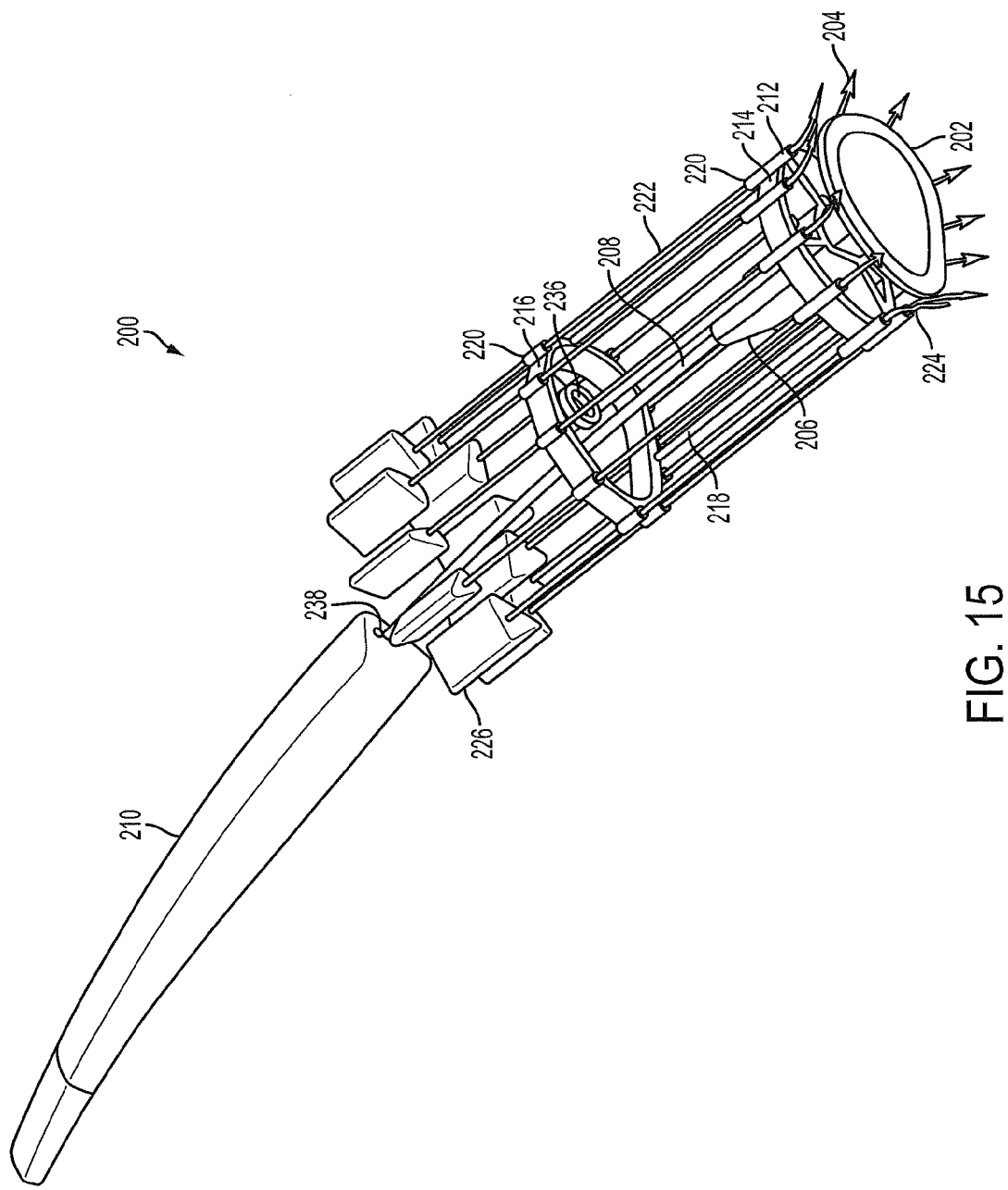
Figure 16:
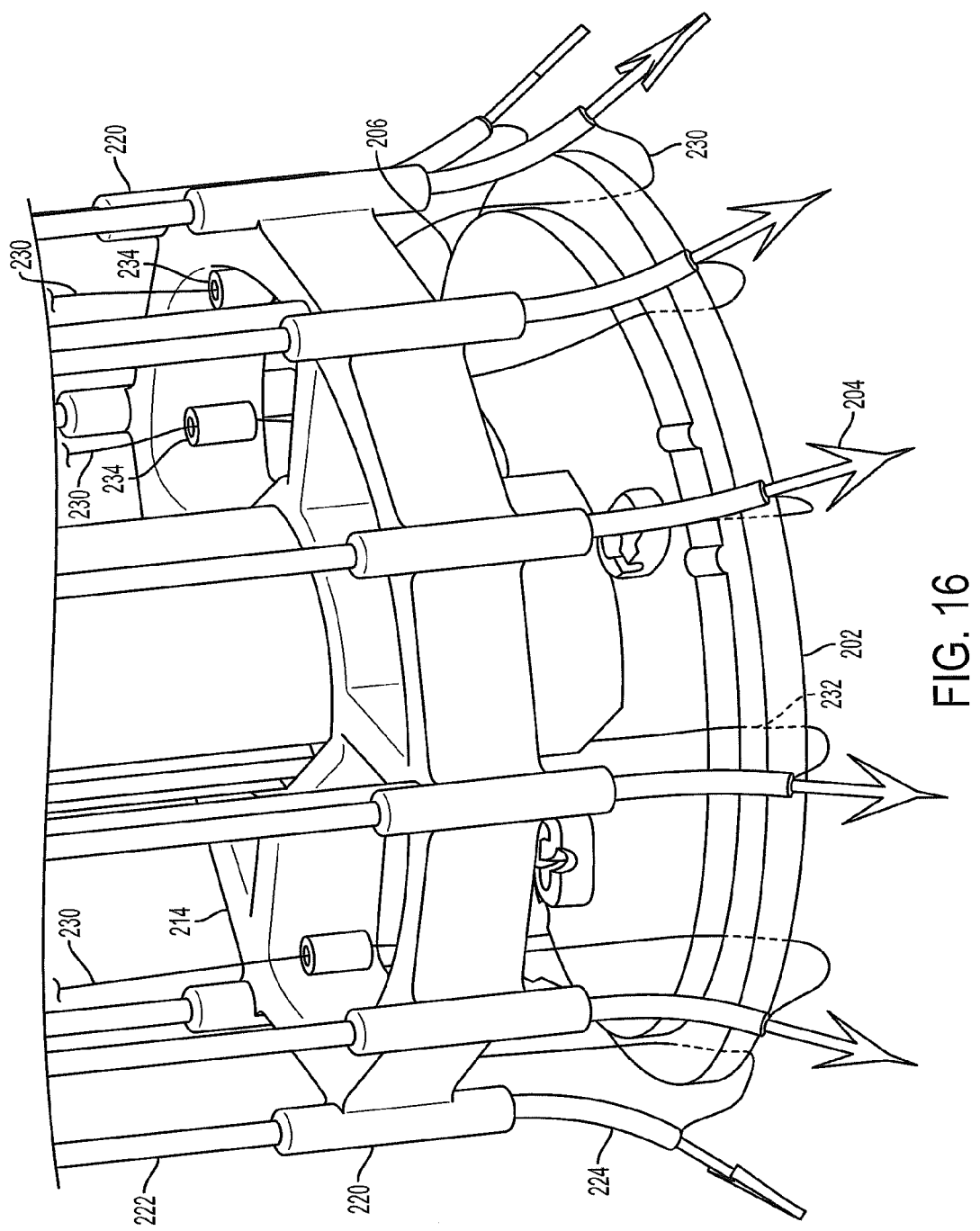

FIGS. 14-16 illustrate an exemplary embodiment of another alternative system 200 for implanting an annuloplasty ring 202 using microanchors 204. The ring 202 and microanchors 204 can be the same as, or similar to, the ring 102 and microanchors 104 described above. The system 200, however, differs from the system 100 in that the system 200 allows all of the spears and microanchors to be introduced into the body at the same time in a bracketed delivery apparatus.

The system 200 can comprise the ring 202 coupled to a ring holder 204. The ring holder 206 can be connected to a holder shaft 208 and a handle 210. The system 200 can further comprise a bracket structure 212 fixed to the ring holder 206. The bracket 212 can comprise a distal bracket 214 and a proximal bracket 216 connected together with struts 218. The distal and proximal brackets 214, 216 can each comprise spear holders 220 disposed around the outer periphery of the brackets configured to hold a plurality of spears 222 in a desired orientation relative to one another and relative to the ring 202. The spear holders 220 can comprise enclosed cylinders that prevent the spears 222 from being removed laterally from the bracket structure 212, or the spear holders 220 can comprise open partial cylinders that allow the spears to be removed laterally, such as with a snap fit. The spear holders 220 can allow the spears 222 to rotate about their longitudinal axes within the spear holders.

As shown, the bracket structure 212 can hold the spears 222 with their distal ends positioned around the perimeter of the ring 202.

Each spear 222 can comprise a rigid or semi-rigid rod or tube, like the spears 106 described above. Similarly, the microanchors 204 can be attached directly to the distal ends 224 of the spears 222 (as shown in FIG. 16) or can be coupled to the distal ends of the spears via adapters similar to the adapters 108. The distal ends 224 of the spears can be curved or bent, such as at about 30° to about 45°. The direction of this curvature relative to the ring 202 can depend on the rotational orientation of the individual spear 222 within the spear holders 220. The distal ends 224 of the spears can hold the microanchors 204 about even with, proximal to, or distal to the ring 202.

The spears 222 can be slidable in along their longitudinal lengths relative to the spear holders 220. The proximal ends 226 of the spears can comprise an enlarged region configured to be gripped, pulled, and/or pushed by a surgeon to move the spears longitudinally distally and/or proximally relative to the bracket structure 212 and the ring 202. Each of the spears 222 can be individually slid proximally and distally such that each of the microanchors 204 can be implanted in the annulus tissue individually. The proximal ends 226 of the spears can also be used to rotate the spears 222 relative to the bracket structure 212 in order to aim the curved distal end 224 and the microanchors 204 as desired. For example, the microanchors 204 can be rotated to point radially inwardly during insertion of the system 200 into the heart, and the rotated to point radially outwardly for insertion of the microanchor into the tissue.

The system 200 also can also comprise sutures 230 (only shown in FIG. 16) attached to the tails of the microanchors 204. The sutures 204 can be threaded from the microanchors 204, up through suture locks 232 in the ring (see FIG. 16) from the distal side of the ring and out through the proximal side of the ring. The suture locks 232, though not shown in detail in FIG. 16, can comprise the same or similar configuration as shown in FIGS. 5-7 and 13. The sutures 230 can have some slack between the microanchors 204 and the suture locks 232 to allow the microanchors to be moved distally for insertion into the tissue.

As shown in FIG. 16, the sutures can extend proximally from the suture locks 232 through guides 234 on the inside of the distal bracket 214. The distal bracket 214 can comprise a different guide 234 for each suture positioned just radially inwardly from the spear holders 220. The sutures 230 can extend proximally from the individual guides 234 through a common guide 236. The common guide 236 can be a portion of the proximal bracket 216 that extends radially inwardly to adjacent the holder shaft 208, and/or the guide 236 can be supported by the holder shaft at about the level of the proximal bracket 216. The collection of sutures 230 can extend proximally from the common guide 236 and through an internal passageway 238 in the handle 210 (see FIG. 15). The passageway 238 can extend through the length of the handle 210 can the free ends of the sutures 230 can extend out from the proximal end of the passageway.

The system 200 can be inserted into the heart with the microanchors 204 and sutures 230 preloaded as described above. The ring 202 can be positioned adjacent to the annulus in an orientation ready for implantation. The spears 222 can then be individually pushed distally and/or rotated in preparation for implanting the respective microanchor 204. With one of the spears 222 extended distally and desirably rotated, the entire system 200 can be moved in the direction in which the microanchor is pointed (e.g., as at about 45° to the longitudinal axis of the system 200), such as by using the handle 210 and/or other surfaces, to drive the microanchor into the tissue. In other methods, the microanchors 204 can be driven into the tissue using the distal sliding motion of the spear 222 relative to the bracket structure 212.

Once the microanchor 204 is implanted in the tissue, the entire system 200 can be moved away from the microanchor to dislodge the tail from the distal end 224 of the spear 222 and then the spear can be retracted proximally and/or rotated relative to the bracket structure to move the empty spear out of the way. The empty spear 222 may alternatively be pulled completely out of the bracket structure 212 and out of the body. Each of the microanchors 204 can be implanted individually, or in groups, in a similar fashion until all of the microanchors are implanted into the tissue.

After the microanchors 204 are implanted in the tissue, the ring holder 214 can be disconnected from the ring 202, such as by cutting sutures coupling the ring to the ring holder. After the ring holder 214 is disconnected, the ring holder, bracket structure 212, spears 222, shaft 208 and handle 210 can be retracted proximally from the ring 202 and out of the body. As these components are retracted, the free ends of the sutures 230 can slide through the passageway 238, the common guide 236 and the individual guides 234. The free ends of the sutures 230, now extending free from the proximal sides of the suture locks 232, can be individually or in groups or collectively pulled proximally relative to the ring 202 to pull the tissue toward the distal side of the suture locks and reshape the annulus as desired. Alternatively, the sutures 230 can be tightened by pulling them relative to the ring 202 before the rest of the system 200 is disconnected from the ring and removed. After the sutures are tightened as desired, the free ends of the sutures can be cut off and removed, which can also occur before or after the other parts of the system 200 are disconnected from the ring 202 and removed.

As mentioned above, the spear holders 220 can comprise enclosed cylinders that constrain the spears 222 from being removed laterally from the bracket structure 212, or the spear holders can be partially open structures that allow the spears to be removed laterally, such as by a snap fit engagement. In the latter case, each spear 222 can be removed from the bracket structure 212 to implant the respective microanchor 204 in a manner similar to that described above regarding the spears 106 of system 100. A surgeon can detach each spear 222 individually from the bracket structure 212 and freehandedly force the microanchor 204 coupled to that spear into the tissue. The spears 222 can be detached from the bracket structure 212 either outside the body or inside the body. In the case where the spears 222 are detached outside of the body, the implantation of the ring 202 can proceed much like as described with regard to the system 100 above. Each microanchor/spear combination can be inserted into the heart one at a time through a relatively smaller incision compared to the incision need to insert the whole system 200 into the heart. After each microanchor 204 is implanted, the respective spear 222 can be removed from the body and discarded, leaving the respective suture 230 extending out of the body to the ring 202. In this case, a sufficient length of suture slack can be provided between the microanchor 204 and the suture lock 232 in the initial configuration of the system 200 because the suture locks 232 do not allow more slack to be easily added later due to their one-way locking mechanism. After all the microanchors 204 are implanted, the ring 202 can be advanced down the sutures 230 to the annulus. The bracket structure 212 can in some embodiments be removed from the ring holder 214 prior to insertion of the ring 202 into the body to reduce bulk and reduce the size of the incision needed. For example, the bracket structure 212 can be slid off over the handle 210 or separated into plural pieces and removed laterally from the ring holder 214. The handle 210 can be used to guide the ring 202 down the sutures 230 into the body to the annulus while the free ends of the sutures are held taught. The ring holder 214 and handle 210 can then be detached from the ring 202 and removed from the body, and the sutures can be tightened as desired and the free ends cut off.

In alternative embodiments, the system 2, the system 100, or the system 200 can include a prosthetic heart valve, such as a prosthetic aortic valve or a prosthetic mitral valve, instead of an annuloplasty ring, and can be used to implant the prosthetic heart valve using the techniques described above.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of this disclosure may be applied, it should be recognized that the illustrated embodiments are only preferred examples and should not be taken as limiting the scope of the inventions. Rather, the scope of the invention is defined by the following claims. We therefore claim all that comes within the scope of these claims.

The invention claimed is:

1. A method of implanting an annuloplasty ring, the method comprising:
   positioning an annuloplasty ring adjacent to the native mitral annulus; and
   after positioning the annuloplasty ring, deploying microanchors into tissue of, or adjacent to, the native mitral annulus, the microanchors being secured to sutures such that the microanchors anchor the sutures to the tissue, and such that the microanchors secure the annuloplasty ring to the tissue via the sutures;

wherein deploying the microanchors comprises pushing the microanchors from a plurality of respective, discrete microanchor holders that pass through or are adjacent to the annuloplasty ring.

2. The method of claim 1, wherein the holders comprise tubes and pushing a respective microanchor comprises moving a plunger within the respective tube such that an end of the plunger pushes the microanchor out of the tube.

3. The method of claim 1, wherein the holders comprise tubes and further comprising pulling the tubes out of the annuloplasty ring after the microanchors are deployed in the tissue and the sutures coupled to the microanchors pass through openings in the ring.

4. The method of claim 1, further comprising pulling the sutures relative to the ring to pull the annular tissue toward the ring to correct the shape of the annulus.

5. The method of claim 4, further comprising securing the sutures to the ring to retain the annular tissue in a corrected shape.

6. The method of claim 5, wherein securing the sutures to the ring comprises advancing clips down the sutures and engaging the clips to the sutures and the ring.

7. The method of claim 4, wherein pulling the sutures comprises pulling the sutures through a plurality of openings in the ring.

8. The method of claim 7, wherein pulling the sutures is performed simultaneously with a single tool.

9. The method of claim 1, wherein positioning the annuloplasty ring adjacent to the native mitral annulus comprises positioning a ring holder coupled to the annuloplasty ring adjacent to the native mitral annulus, the ring holder comprising a plurality microanchor holder guides configured to guide the microanchor holders and a plurality of suture guides configured to guide the sutures from the annuloplasty ring through the ring holder.

10. A method of implanting an annuloplasty ring, the method comprising:

positioning an annuloplasty ring adjacent to the native mitral annulus; and after positioning the annuloplasty ring, deploying microanchors into tissue of, or adjacent to, the native mitral annulus to secure the annuloplasty ring to the tissue, the microanchors being secured to sutures, wherein deploying the microanchors comprises pushing the microanchors out of a plurality of respective, discrete microanchor tubes that pass through the annuloplasty ring; and pulling the tubes out of the annuloplasty ring after the microanchors are deployed in the tissue and sutures coupled to the microanchors pass through openings in the ring.

11. The method of claim 10, the method further comprises pulling the sutures relative to the ring to pull the annular tissue toward the ring to correct the shape of the annulus.

12. The method of claim 11, wherein pulling the sutures comprises pulling the sutures through a plurality of openings in the ring.

13. The method of claim 11, wherein pulling the sutures is performed simultaneously with a single tool.

14. The method of claim 10, wherein the microanchors are secured to respective sutures and the method further comprises securing the sutures to the ring to retain the annular tissue in a corrected shape.

15. The method of claim 14, wherein securing the sutures to the ring comprises advancing clips down the sutures and engaging the clips to the sutures adjacent the ring.

16. A method of implanting an annuloplasty ring, the method comprising:

positioning an annuloplasty ring adjacent to the native mitral annulus; and after positioning the annuloplasty ring, deploying microanchors into tissue of, or adjacent to, the native mitral annulus to secure the annuloplasty ring to the tissue, the microanchors being secured to sutures, wherein deploying the microanchors comprises pushing the microanchors out of a plurality of respective, discrete microanchor holders that pass through or are adjacent to the annuloplasty ring;

wherein positioning the annuloplasty ring adjacent to the native mitral annulus comprises positioning a ring holder coupled to the annuloplasty ring adjacent to the native mitral annulus, the ring holder comprising a plurality microanchor holder guides configured to guide the microanchor holders, the ring holder further comprising a plurality of suture guides configured to guide the sutures from the annuloplasty ring through the ring holder.

17. The method of claim 16, further comprising pulling the sutures through a plurality of openings in the ring to pull the annular tissue toward the ring to correct the shape of the annulus.

18. The method of claim 17, wherein pulling the sutures is performed simultaneously with the ring holder.

19. The method of claim 16, further comprising advancing clips down the sutures and engaging the clips to the sutures adjacent the ring to secure the sutures to the ring to retain the annular tissue in a corrected shape.

20. A method of implanting an annuloplasty ring, the method comprising:

positioning an annuloplasty ring adjacent to the native mitral annulus; and after positioning the annuloplasty ring, deploying microanchors into tissue of, or adjacent to, the native mitral annulus to secure the annuloplasty ring to the tissue, wherein deploying the microanchors comprises pushing the microanchors out of a plurality of respective, discrete microanchor tubes that pass through the annuloplasty ring;

wherein pushing the microanchors out of the tubes comprises moving plungers within the tubes such that ends of the plungers push the microanchors out of the tubes, the plungers being separate from the microanchors.

21. The method of claim 20, further comprising pulling the plungers and the tubes out of the annuloplasty ring after the microanchors are deployed in the tissue.

* * * * *